(12) United States Patent
Martinez-Martin et al.

(10) Patent No.: US 10,545,169 B2
(45) Date of Patent: Jan. 28, 2020

(54) TOP-COVER FOR A CONTROLLED ENVIRONMENTAL SYSTEM, TOP-COVER-SET AND CONTROLLED ENVIRONMENTAL SYSTEM COMPATIBLE WITH PROBE BASED TECHNIQUES AND PROCEDURE TO CONTROL THE ENVIRONMENT FOR A SAMPLE

(71) Applicants: Universität Basel, Basel (CH); ETH Zurich, Zurich (CH)

(72) Inventors: David Martinez-Martin, Basel (CH); Daniel J. Mueller, Basel (CH); Sascha Martin, Basel (CH); David Alsteens, Allschwil (CH); Gotthold Flaschner, Freiburg (DE)

(73) Assignees: ETH ZURICH, Zurich (CH); UNIVERSITÄT BASEL, Basel (CH)

( * ) Notice: Subject to any disclaimer, the term of this patent is extended or adjusted under 35 U.S.C. 154(b) by 0 days.

(21) Appl. No.: 15/746,717

(22) PCT Filed: Jul. 15, 2016

(86) PCT No.: PCT/EP2016/001243
§ 371 (c)(1),
(2) Date: Jan. 22, 2018

(87) PCT Pub. No.: WO2017/012708
PCT Pub. Date: Jan. 26, 2017

(65) Prior Publication Data
US 2018/0224479 A1   Aug. 9, 2018

(30) Foreign Application Priority Data

Jul. 22, 2015  (EP) ..................................... 15002176

(51) Int. Cl.
*G01Q 30/14* (2010.01)
*C12M 1/00* (2006.01)
(Continued)

(52) U.S. Cl.
CPC ............. *G01Q 30/14* (2013.01); *C12M 23/38* (2013.01); *C12M 41/14* (2013.01); *G01Q 60/38* (2013.01); *G01Q 70/02* (2013.01)

(58) Field of Classification Search
CPC ........ G01Q 30/14; G01Q 70/02; G01Q 60/38; G01Q 30/12; C12M 41/14; C12M 23/38
(Continued)

(56) References Cited

U.S. PATENT DOCUMENTS 6,051,825 A * 4/2000 Lindsay .................. G01Q 30/14
                                                              250/201.3
6,437,328 B1 * 8/2002 Knauss .................. B82Y 35/00
                                                              250/307

(Continued)

FOREIGN PATENT DOCUMENTS

ES       2351742 A1    2/2011
WO   2010/062654 A2    6/2010

OTHER PUBLICATIONS

European Patent Office—International Preliminary Report on Patentability, dated Jan. 23, 2018.

*Primary Examiner* — Michael Maskell
(74) *Attorney, Agent, or Firm* — Michael J. Brown

(57) ABSTRACT

The invention relates to a top-cover for a controlled environmental system (CES) for use with a measurement technique that requires introducing a probe to a sample placed on a sample holder, a CES and a procedure to control the environment for a sample in a system in particular a CES during a measurement with a probe based technique.

15 Claims, 2 Drawing Sheets

Figure 1:
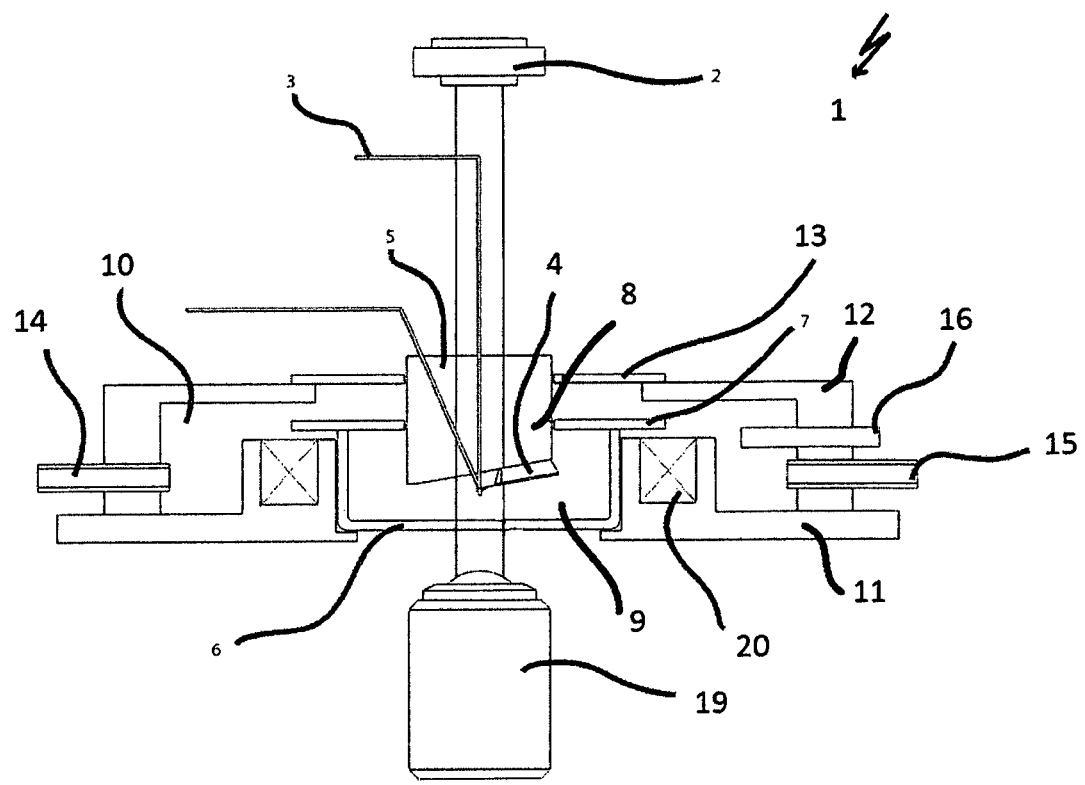

(51) Int. Cl.
*G01Q 60/38* (2010.01)
*G01Q 70/02* (2010.01)

(58) Field of Classification Search
USPC .............................................. 250/12, 14, 18
See application file for complete search history.

(56) References Cited

U.S. PATENT DOCUMENTS

| | | | |
|---|---|---|---|
| 6,490,913 B1 * | 12/2002 | Martin | B82Y 35/00 73/105 |
| 2005/0241392 A1 | 11/2005 | Lyubchenko | |
| 2006/0043289 A1 * | 3/2006 | West | G01Q 30/14 250/309 |
| 2007/0234829 A1 | 10/2007 | Pirsch | |
| 2015/0192604 A1 * | 7/2015 | Yamamoto | G01Q 30/02 850/18 |
| 2015/0338438 A1 * | 11/2015 | Viani | G01Q 10/00 850/18 |
| 2016/0003867 A1 * | 1/2016 | Tseng | G01Q 30/12 850/14 |

* cited by examiner

TOP-COVER FOR A CONTROLLED ENVIRONMENTAL SYSTEM, TOP-COVER-SET AND CONTROLLED ENVIRONMENTAL SYSTEM COMPATIBLE WITH PROBE BASED TECHNIQUES AND PROCEDURE TO CONTROL THE ENVIRONMENT FOR A SAMPLE

The invention relates to a top-cover for a controlled environmental system (CES) for use with a measurement technique that requires introducing a probe to a sample placed on a sample holder, a top-cover-set, a CES and a procedure to control the environment for a sample in a system in particular a CES during a measurement with a probe based technique e.g. a scanning probe microscopy technique.

Sample holders compatible with scanning probe microscopy techniques which in particular allow keeping living biological systems, as for instance adhering or floating cells, in a cell culture dish are known from the state of the art.

The atomic force microscopy (AFM) has not stopped developing since its invention. In addition to the topography, the AFM is able to measure other physical, chemical or biological properties of a sample. Its capability to work in liquid environments makes AFM a very useful tool to address many questions in cell biology. However, the lack of sample holders to keep living cells under the conditions of a cell incubator while being explored by probe based techniques, limits importantly the type of experiments that can be done as well as the type of cells that can be studied.

Cells require a medium to be cultured, which is usually a liquid or a gel. Appropriate culture or growth media are fundamental for the performance of the cell culture. Generally, growth media contain aminoacids, vitamins, inorganic salts, sugars, hormones, etc in order to provide nutrients together with important compounds for the cells to go through the cell cycle. In addition, cells demand a specific pH to keep the enzymatic activity, which requires having a system to regulate the pH of the media. For this reason, as a major component, culture media contain a buffer. There are two main options to buffer media:

1.—The main strategy to maintain the pH of the media is by using a balanced salt solution, usually sodium bicarbonate, together with a gas phase that contains approximately 5% $CO_2$ and 95% air. In order to prevent the evaporation of the culture medium, the recipients containing the cells are sealed but allowing the interchange of $CO_2$ and $O_2$. In addition the gas mixture is preferably humidified reaching approximately 95% relative humidity. This is for instance a very common configuration for cell culture incubators.

2.—An alternative to the previous method is to use culture media to regulate the pH that does not require a special $CO_2$ atmosphere. A frequent example is media containing HEPES.

However, both strategies present severe problems when the cell culture has to be mounted in an AFM or a similar instrument, which requires to introduce a probe in the culture dish. The main problems are:

For the strategy 1:

The osmolarity of the media changes within minutes due to progressive evaporation or addition of water from or to the media, leading cells to stress and finally to death. This effect, in the current configuration of all AFM based systems, results as a consequence of the introduction of dry or humidified gas mixture directly over the media. Usually the sample holder comprises a small chamber or fixation system where the culture dish or sample is placed. The chamber allows the probe of the device (for instance an AFM cantilever) to get into the dish. To conduct the gas mixture over the media, the sample holder contains an inlet. In addition, the sample holder contains an outlet to avoid overpressures. To minimize the evaporation of water, the gas mixture can be humidified close to water saturation or approximately 95% relative humidity. But even in these conditions, evaporation remains still important and it is very difficult to reach a steady state. If the gas mixture is saturated of humidity or oversaturated some water can condense into the culture dish changing the water content and/or osmolarity.

For the strategy 2:

HEPES or equivalents compounds can be toxic for the cells, limiting importantly the time cells can survive with this type of buffer. In addition, has been shown that HEPES becomes photo-toxic when exposed to ambient light and in particular to light used with modern optical techniques such as fluorescence, DIC (differential interference contrast), phase contrast, etc. However, those techniques are fundamental to characterize cell state and morphology.

It is an object of the invention to improve these known devices.

According to a first aspect of the invention, a solution to this technical problem is achieved by providing a top-cover for a CES for use with a measurement technique that requires introducing a probe to a sample placed on a sample holder wherein the top-cover comprises a cavity, which is forming a chamber around the sample on the sample holder. When the top-cover is placed on a sample holder for forming a CES the cavity is closed with the sample holder to form a chamber comprising the sample on the sample holder, or closed with the sample holder and probe holder to form a chamber comprising the sample on the sample holder.

Preferably the cross section of the cavity is U-shaped. However, also other shapes like a triangular shape are possible.

The cavity in the top cover preferably comprises an inlet and/or an outlet. The inlet can be used to introduce the gas mixture and the outlet can be used to prevent overpressures. Inlet and outlet are not function specific and can also be used with the opposite function. Also, multiple inlets and/or outlets are possible. However, a placement of inlet and outlet in the sample holder is also possible.

The cavity in the top-cover can comprise a humidity sensor. It can be used to monitor the relative humidity within the chamber when the top-cover is placed on the sample holder to form a CES. In addition, the information from the sensor can be used to actively control the humidity within the chamber. However, a placement of the humidity sensor in the sample holder is also possible.

The cavity in the top-cover can contain a port that connects the exterior of the top cover to the sample. This allows for introducing and exchanging fluids and/or gases during the measurement process in the sample. However, a placement of the port in the sample holder is also possible.

The top-cover preferably comprises a lid with an aperture for the probe holder to go through. This has the advantage that the lid can be taken off to allow for direct access to the sample.

Preferably, the lid is constructed separately. If the lid with the aperture is built in a separated piece from the top-cover body and only is in connection with the top-cover body by a non-positive connection, the lid allows sliding according to the relative movement of the probe with respect to the culture dish without compromising the sealing. This allows the probe to reach different locations on the sample.

Further preferably, the aperture fits by non-positive mechanical engagement with the probe holder. When the top-cover is placed on the sample holder to form a CES, the size of the aperture can be such, that when the probe goes through, the chamber is sealed well enough avoiding evaporation of water content but allowing the $CO_2$ and $O_2$ to go through. However, under certain circumstances i.e. when the lid forms the connection to the exterior, it can be preferred that the lid fits well enough with the probe holder to reduce gas leaks more thoroughly but still allowing the probe holder to go in and out. Also a positive mechanical engagement can be advantageous individually or in combination with the non-positive engagement.

A second aspect of the invention relates to a top-cover-set comprising a top-cover according to the present invention and a separation element that divides the cavity into two chambers. The separation element can be any element that is suitable to achieve the separation in two chambers like a separate second top-cover, a ring that connects the sample holder and the first lid or a second lid only, if the sample holder is e.g. a petri dish. Yet, it is not limited to that.

A third aspect of the invention relates to a CES comprising a top-cover according to the present invention or a top-cover-set according to the present invention and a sample holder.

Preferable the CES comprises a first chamber to accommodate the sample on the sample holder and a second chamber to accommodate a suitable gas mixture to regulate the environment in the first chamber.

The first and the second chamber can be interconnected in particular to allow for a gas exchange between the first and the second chamber. While a connection at the top-cover is advantageous, it is also possible that a connection between the first and the second chamber is achieved by a connection over the sample holder. The connection is e.g. possible through leaking at the separation element in particular a lid, via extra channels or by using selectively permeable materials at the separation or interphase between the chambers.

Preferably, the second chamber is adjacent to the first chamber. By placing the top-cover or the top-cover-set on the sample holder, two adjacent chambers can be formed. If the first chamber provides a suitable environment in form of a certain gas mixture for the sample (located in it), an exchange with the adjacent second chamber, which contains a suitable gas mixture to maintain the environment in the first chamber, will provide a more stable environment in the first chamber.

Preferably, the second chamber is concentrically arranged around the first chamber. Like this, the first chamber is completely surrounded by the second chamber. This has the advantage that an exchange is possible around the full circumference of the first cavity thereby allowing for a homogeneous environment in the first chamber.

In particular the sample holder can be a culture dish holder. This allows for use of the CES with a measurement technique that requires introducing a probe into a cell culture dish for a living sample.

Living biological samples can mean in particular cells. As for instance, adherent or suspended cells.

Preferably, a first lid with a first aperture for the probe holder to go through and a cell culture dish form a first chamber. This has the advantage that the lid can be taken off to allow for direct access to the sample.

The second chamber can be formed by the body of the top-cover and a first lid and/or a second lid with a second aperture for the probe holder to go through. This has the advantage that the lid/lids can be taken off to allow for direct access to the sample.

Preferably, both lids are constructed separately. If the lids with the apertures are built in separated pieces and only are in connection with the top-cover body and/or the Petri dish by a non-positive connection, these lids allow sliding according to the relative movement of the probe with respect to the culture dish without compromising the sealing. This allows the probe to reach different locations on the sample.

Preferably, the first and/or the second aperture fit by non-positive mechanical engagement with the probe holder. The same applies if there is only one lid. In the case of the first lid, the size of the aperture is such, that when the probe goes through, the first chamber is sealed well enough avoiding evaporation of water but allowing the $CO_2$ and $O_2$ to go through. In case of the second lid, the second aperture equally can have size for the probe to go through to allow for a same level of sealing. However, under certain circumstances i.e. when only one lid is used or when the second lid forms the connection to the exterior, it can be preferred that the lid or lids fit well enough with the probe holder to reduce gas leaks but allowing the probe holder to go in and out. Also a positive mechanical engagement can be advantageous individually or in combination with the non-positive engagement.

Preferably, the CES for a sample in a cell culture dish for use with a measurement technique that requires introducing a probe into a cell culture dish comprising a top-cover in particular according to the invention, and a sample holder with a first lid for the probe holder to go through and a second lid with a second aperture for the probe holder to go through, wherein the cell culture dish in the sample holder and the first lid form a first chamber. The body of the top cover, the second lid and the sample holder form a second chamber. If the probe holder is not introduced in the aperture, the chamber comprises an opening The CES can have the second chamber adjacent to the first chamber, which contains a suitable gas mixture in order to regulate the pH of the culture media. The gas mixture is preferably humidified between 80% and 100% relative humidity.

This allows keeping living biological systems, as for instance adherent or suspended cells under incubation conditions for long periods meanwhile the probe holder is introduced. The CES prevents evaporation of the medium where the biological systems are in. At the same time it allows to regulate the pH of the medium by flowing a gas mixture.

The second chamber can be simplified by reducing the gap between the top cover and the first lid allowing to use the first lid for both chambers. Also other configurations can be used containing only one lid. This has the advantage, that structural complexity is reduced. However, in this configuration gas exchange between the two chambers is only possible through the gap between the cell culture dish and the first lid. In the preferred solution gas exchange is additionally possible through the gap between the first lid and the probe holder. However, it is also possible that a connection between the first and the second chamber is achieved by a connection over the sample holder.

The second chamber preferably contains an inlet and/or an outlet. The inlet can be used to introduce the gas mixture and the outlet can be used to prevent overpressures. Inlet and outlet are not function specific and can also be used with the opposite function. Also, multiple inlets and/or outlets are possible.

The second chamber can comprise a humidity sensor. It can be used to monitor the relative humidity within the second chamber. In addition, the information from the sensor can be used to actively control the humidity within the second chamber.

The CES can contain a port that connects the exterior to the first chamber. This allows for introducing and exchanging fluids during the measurement process in the first chamber, i.e. in the Petri dish. This port can be located in the top-cover and/or the sample holder.

These elements i.e. the inlet/outlet, sensor and/or the port can be in the probe holder or the probe itself.

Preferably, the first or the second and/or the second aperture fit by non-positive mechanical engagement with the probe holder. In the case of the first lid, the size of the aperture is such, that when the probe goes through, the first chamber is sealed well enough avoiding evaporation of water content but allowing the $CO_2$ and $O_2$ to go through. In case of the second lid, the second aperture equally can have size for the probe to go through to allow for a same level of sealing. However, under certain circumstances i.e. when only one lid is used or when the second lid form the connection to the exterior, it can be preferred that the lid fits well enough with the probe or probe holder to reduce gas leaks. Alternatively or additionally a connection via positive mechanical engagement can be advantageous.

According to a further preferable feature, the CES is compatible with optical techniques. Optical techniques can be fluorescence, differential interference contrast (DIC), phase contrast, confocal microscopy, and related techniques, in general, all those based on an inverted microscope. This is achieved by the culture dish being located in an accessible way with an inverted microscope. Additionally, optical access can be reached from top due to the apertures.

The CES can also incorporate a heating/cooling system in order to keep the sample at a specific temperature.

To sum up in order to regulate the pH and osmolarity of the culture, the proposed device works according to the strategy 1 described in the state of the art. However, the proposed device represents a big improvement over the state of the art since it allows keeping the cells under incubation conditions for a longer time (several days) than the previous devices (several hours), while being mounted on an AFM or any other instrument that requires to introduce the probe into the sample.

A forth aspect of the invention relates to a process to control the environment for a sample in a system in particular a controlled environmental system according to the invention for use with a measurement technique that requires introducing a probe to a sample placed on a sample holder wherein, the sample is located in a first chamber and a second chamber is filled with a suitable gas mixture regulating environment in the first chamber. In particular when the sample is a biological sample in a culture dish in a culture media the pH and osmolarity of the culture media can be regulated. A humidity sensor or other sensors can be used to measure the status in the first and or the second chamber and the parameters in both chambers can be regulated accordingly.

Preferably the gas mixture is humidified between 80% and 100% relative humidity.

The invention will be described in more detail herein after with reference to an exemplary embodiment. In the drawing, FIG. 1 shows a schematic representation of a CES and FIG. 2 shows a schematic representation of a CES with an additional port.

Figure 2:
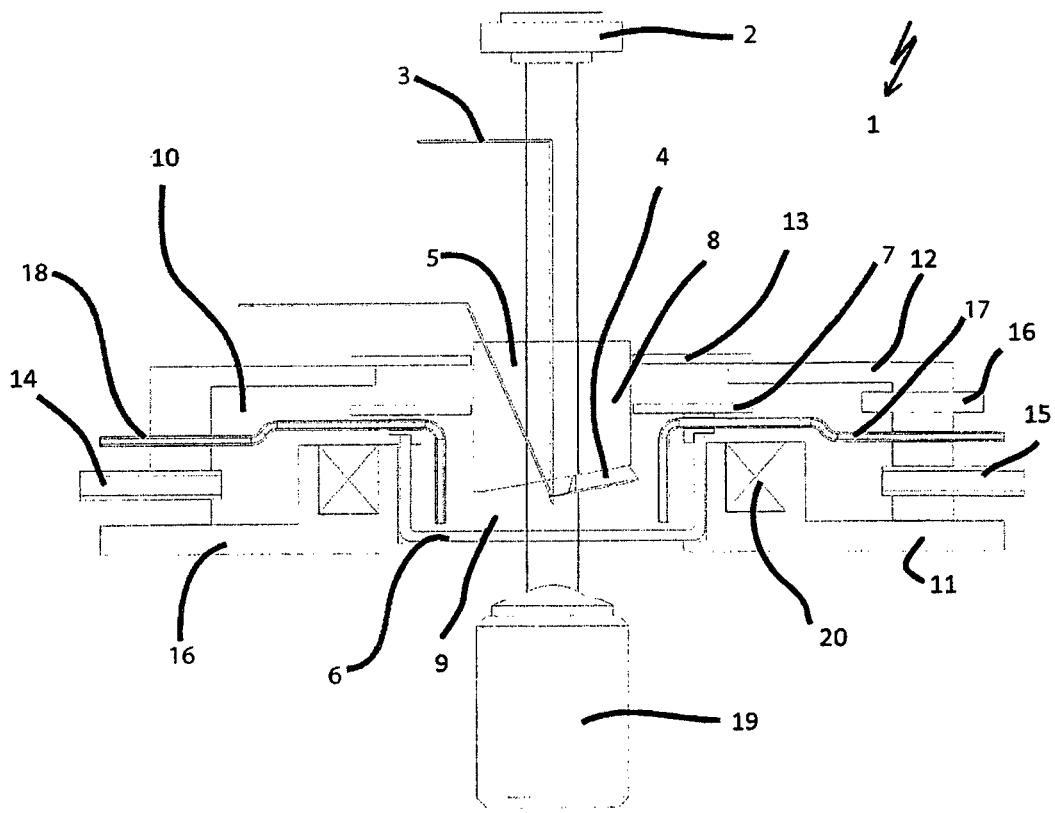

The CES 1 in FIG. 1 is shown with a light source 2 for differential interference contrast, phase contrast or an equivalent technique. Furthermore, a laser 3 is shown to read the movement of the cantilever 4 which is used as a probe of an AFM and held by the cantilever holder 5 for an AFM-based technique compatible with optical microscopy techniques. However, other types of probes and/or holders can be compatible with the device. This is just an example to show, that the device is compatible with these types of techniques or any other that requires to introduce a probe into the sample or chamber where the sample is placed.

The sample holder 11 of the CES 1 holds a Petri dish 6 in which the sample is placed in a buffer solution. This Petri dish 6 is covered by the first lid 7 with an aperture 8 for the cantilever holder 5 to go through. The Petri dish 6 together with the cantilever holder 5 and the lid 7 form the first chamber 9. The lid 7 can move allowing different positions of the cantilever holder 5 with respect to the Petri dish 6. The cantilever holder 5 can be moved in and out through the lids 7 and 13. The second chamber 10 is formed by a sample holder 11 of the CES 1, a top-cover 12, the cantilever holder 5, the first lid 7 and the second lid 13. The second chamber 10 is the chamber into which the gas mixture is introduced. The gas mixture can be used to control the pH and osmolarity of the buffer solution located in the first chamber 9. Also, the lid 13 has an aperture for the cantilever holder 5 to go through. The second chamber 10 has an inlet 14 that can be used to pump the gas mixture into the second chamber 10. The outlet 15 can be used to avoid overpressures within said second chamber 10. Alternatively, the function of inlet 14 and outlet 15 can be switched and the outlet 15 can be used to pump the gas mixture into the second chamber 10 or the inlet 14 can be used in order to avoid overpressures within said second chamber 10. The humidity sensor 16 can be used to monitor the relative humidity within the second chamber 10. In addition, the information from the sensor 16 can be used to actively control the humidity within the second chamber 10.

The system is compatible with an inverted microscope 19 and techniques based on that such as fluorescence, DIC, phase contrast, confocal microscopy and others. Additionally optical access from the top is possible.

Between the sample holder 11 and the top cover a sealing (not shown) can be provided.

The setup of the CES 1 in FIG. 2 is identical. However, additionally ports 17, 18 are provided, that connect the exterior of the CES 1 with the first chamber 9. These ports 17,18 can be used to exchange the fluidic medium of the petri dish 6 or to deliver desired substances.

A heating and or cooling system 20 allows keeping the sample at a desired temperature.

The invention claimed is:

1. Top-cover for a controlled environmental system for use with a measurement technique that requires introducing a probe to a sample placed on a sample holder wherein the top-cover comprises a cavity which is forming a chamber around the sample on the sample holder, when placed on the sample holder, and wherein the top-cover comprises a lid with an aperture for a probe holder to go through, wherein the lid is in connection with the top-cover by a non-positive connection, wherein the lid is constructed separately, and wherein the aperture fits by non-positive mechanical engagement with the probe holder.

2. Top-cover according to claim 1, wherein the cavity in the top-cover comprises an inlet and/or an outlet.

3. Top-cover according to claim 1, wherein the cavity in the top-cover comprises a humidity sensor.

4. Top-cover according to claim 1, wherein the cavity in the top-cover comprises a port that connects an exterior of the top-cover to the sample.

5. Top-cover-set comprising a top-cover according to claim 1 and a separation element that divides the chamber into two chambers.

6. Controlled environmental system comprising a top-cover according to claim 1 and a sample holder.

7. Controlled environmental system according to claim 6 comprising a first chamber to accommodate the sample on the sample holder and a second chamber to accommodate a suitable gas mixture to regulate the environment in the first chamber.

8. Controlled environmental system according to claim 7 wherein the first and the second chamber are connected.

9. Controlled environmental system according to claim 7, wherein the second chamber is concentrically arranged around the first chamber.

10. Controlled environmental system according to claim 6, wherein the sample holder is a culture dish holder and a first lid with a first aperture for the probe holder to go through and a cell culture dish form a first chamber.

11. Controlled environmental system according to claim 10 wherein the body of the top-cover and a first lid and/or a second lid with a second aperture for the probe holder to go through form a second chamber.

12. Controlled environmental system according to claim 6, wherein the system comprises a heating and/or cooling system.

13. Controlled environmental system according to claim 6, wherein the controlled environmental system is compatible with at least one of the following optical techniques: fluorescence, differential interference contrast (DIC), phase contrast, confocal microscopy, and related techniques based on an inverted microscope.

14. Process to control the environment for a sample in a controlled environmental system according to claim 6 for use with a measurement technique that requires introducing a probe to a sample placed on a sample holder, wherein the sample is located in a first chamber and a second chamber is filled with a suitable gas mixture regulating environment in the first chamber.

15. A controlled environmental system, comprising:
a sample holder,
a first chamber to accommodate a sample on the sample holder and
a second chamber to accommodate a suitable gas mixture to regulate the environment in the first chamber,
wherein the controlled environmental system comprises a top-cover comprising a cavity which is forming the second chamber, when placed on the sample holder around the first chamber, wherein the top-cover enables introducing a probe to the sample on the sample holder,
and wherein the top-cover comprises a lid with an aperture for a probe holder to go through, wherein the lid is in connection with the top-cover by a non-positive connection, wherein the lid is constructed separately, and wherein the aperture fits by non-positive mechanical engagement with the probe holder.

* * * * *